United States Patent [19]

Neumann

[11] Patent Number: 4,968,295
[45] Date of Patent: Nov. 6, 1990

[54] METHOD OF SEPARATING THE CONSTITUENTS OF THE BLOOD

[75] Inventor: Hans-Jürgen Neumann, St. Wendel, Fed. Rep. of Germany

[73] Assignee: Fresenius Ag, Bad Homburg von der Hole, Fed. Rep. of Germany

[21] Appl. No.: 99,289

[22] Filed: Sep. 21, 1987

[30] Foreign Application Priority Data

Sep. 22, 1986 [DE] Fed. Rep. of Germany ....... 3632176

[51] Int. Cl.$^5$ .............................................. A61M 5/00
[52] U.S. Cl. .......................................... 604/6; 604/4; 210/782; 364/502; 494/6; 494/10
[58] Field of Search ............... 604/5, 6; 364/496, 500, 364/502; 494/6, 10, 27, 38, 42; 210/781, 782; 436/45

[56] References Cited

U.S. PATENT DOCUMENTS

| | | | |
|---|---|---|---|
| 3,655,123 | 4/1972 | Judson et al. | 604/6 |
| 4,151,844 | 5/1979 | Cullis et al. | 604/6 |
| 4,185,629 | 1/1980 | Cullis et al. | 604/6 |
| 4,187,979 | 2/1980 | Cullis et al. | 604/6 |
| 4,447,191 | 5/1984 | Bilstad et al. | 604/6 |
| 4,458,539 | 7/1984 | Bilstad et al. | 604/6 |
| 4,464,167 | 8/1984 | Schoendorfer et al. | 604/6 |
| 4,481,827 | 11/1984 | Bilstad et al. | 604/6 |

*Primary Examiner*—Robert A. Wax
*Assistant Examiner*—T. J. Wallen
*Attorney, Agent, or Firm*—Townsend and Townsend

[57] ABSTRACT

The invention relates to the control of a system in a blood centrifuge for separating the constituents (fractions) of the whole blood taken from a donor "in vivo" and provided with anticoagulants. A control is provided which as input quantity includes a signal on the flow rate of the full blood and on the output side is connected to the speed setting means for the blood centrifuge. The transfer function of the control is so defined that on a change of the full blood flow the speed of rotation is set so that the volume ratios of the blood fractions to the full blood remain constant. Preferably, the output signal of the control is proportional to the square root of the full blood flow. The control is preferably formed by a microprocessor.

16 Claims, 3 Drawing Sheets

METHOD OF SEPARATING THE CONSTITUENTS OF THE BLOOD

BACKGROUND OF THE INVENTION

The invention relates to a method of separating the constituents of the blood (full blood) which is taken adjustably from a donor "in vivo", adjustably mixed with anticoagulants supplied to a speed-adjustable blood centrifuge from which the separated constituents (blood fractions) are adjustably withdrawn and thereafter partly collected and partly returned to the donor, wherein the flow rates of the full blood and of the fractions are measured and automatically adjusted so that an optimum separation takes place.

The invention further relates to an apparatus for carrying out the method.

In separating systems of this type it is important for the flows of the full blood and the blood fractions to be in a correct ratio to each other and the fractions to include to a great extent only the separated constituent, i.e. the so-called separating boundary (the boundary between red blood corpuscles and the other fractions) in the blood centrifuge to be located at an optimum position.

A separating system of the aforementioned type is known from U.S. Pat. No. 3,489,145 and explained in all details therein.

The control arrangements provided in the known case for the apparatuses setting the flow rates (and including in particular delivery pumps) and the speed of rotation regulator of the centrifuge permit a separate setting of the flow rates of the associated delivered media and a speed of rotation setting of the centrifuge to take account of the aforementioned conditions.

Associated with the centrifuge is a buffer container for the full blood provided with anticoagulants, said container having a level control which automatically interrupts the supply of full blood when a predetermined amount of full blood is disposed in the buffer container.

In spite of this partial automation (level control) a disadvantage in the known case is that it is left to the operator to actuate the control or regulating means to ensure an optimum setting and retain this setting over longer periods of time (subsequent adjustment). The operator visually supervises the separating boundary. At a given speed of rotation of the centrifuge via a change of the delivery speed of the individual blood fractions with respect to each other, i.e. a change of the speeds of rotation of the associated pumps, the separating boundary can be displaced (column 11, line 64, to column 12, line 3, of the U.S. patent).

This latter context is utilized in the system according to further known U.S. Pat. No. 4,151,844. A photoelectric sensing is provided which optically detects the location of the separating boundary and converts it to an electrical signal which is compared with a desired value; the difference acts via a digital controller on a positioning member which oppositely alters the setting of the means for transporting the fractions in dependence upon the magnitude and amount and direction of the rise of the optical density at the separating boundary.

The aforementioned U.S. patent does not given any details on the control of the other apparatus and the centrifuge itself.

This known principle of automatic regulation of the separating boundary as controlled variable via a photoelectric ratio control of the flow rates of the withdrawn fractions has the considerable disadvantage that it does not include the other variable system parameters in the automatic control. Fluctuations in the full blood supply and the centrifuge speed of rotation can thus only be eliminated in unsatisfactory manner. Furthermore, the system setting possibilities (variation width of the setting possibilities in the system) are considerably limited.

DE-OS No. 2,845,399 discloses a further separating system, that set forth at the beginning from which the invention proceeds.

In this system the system known from the first mentioned U.S. Pat. No. 3,489,145 has been practically automated such that at a predetermined speed of rotation the flow rates of the full blood and of the fractions are set with respect to each other so that an optimum separation is effected in dependence upon the response of an optical sensor on mixing the fractions (hematocritic supervision analogous to the second U.S. patent mentioned). In the known separating system the centrifuge is set to a predetermined speed of rotation so that with a full blood flow set as desired specific fraction volumes occur whose unmixed withdrawal must be controlled and monitored by the automatic control system. The withdrawal speeds of the fractions necessary for unmixed separation must therefore be determined, i.e. it is necessary for a given speed and given full blood flow to determine the proportion of the individual fractions and set the withdrawal corresponding to said determination. On any change of the full blood flow the known system must therefore carry out a complete new determination of the fractions occurring.

Thus, in the known case long control times result and it is therefore not possible to set the full blood flow very rapidly in accordance with the donor or blood pressure or even change it during a separation. Moreover, in extremely unfavourable cases it may even happen that the speed of rotation of the centrifuge has been so unfavourably selected for the selected full blood flow that one of the desired fractions does not accumulate at all and thus cannot be withdrawn.

SUMMARY OF THE INVENTION

The problem underlying the invention is to improve the method and associated apparatus referred to at the beginning so that the full blood flow can be varied very rapidly.

According to the invention as regards the method this problem is solved in that on a variation of the full blood flow the speed of rotation of the centrifuge is variable in such a manner that the ratio of the volume parts of the blood fractions separated in the centrifuge per unit time to the volume of the full blood introduced into the centrifuge in the unit time is approximately the same ratio before and after a change of the full blood flow.

As regards the apparatus for controlling a system for separating the constituents of the blood (full blood) withdrawn from a donor "in vivo" corresponding to this method the solution of the aforementioned problem proceeding from an apparatus having at least one blood centrifuge with which means are associated for blood withdrawal, delivery of anticoagulants, of the removed blood to the blood centrifuge and of the separated constituents (blood fractions) which are partially collected and partially returned to the donor, control/regulating means for adjusting the flow rates of the anticoagulant, the full blood and the various blood fractions and the speed of rotation of the centrifuge, and a sensor for detecting the flow rate of the full blood, the signal of which is switched to a control stage whose output is connected to the control/regulating means is achieved in that the transfer function of the control stage is so defined that on a change in the full blood flow the speed of rotation of the centrifuge is variable in such a manner that the ratio of the volume parts of the blood fractions separated in the centrifuge per unit time to the volume of the full blood conveyed in the unit time into the centrifuge is approximately the same ratio before and after a change in the full blood flow.

In the separating system according to the invention on a change in the full blood flow the centrifuge speed is also changed in the "correct ratio", said "correct ratio" being defined by a transfer function, i.e. the transfer function controls the accumulation of the individual fractions.

The transfer function need not be an analytically predetermined function; it may also be an empirically determined function.

At a desired full blood flow by the correct setting of the speed of rotation to said full blood flow the optimum accumulation of the fractions is therefore predetermined so that the necessary withdrawal speeds for all fractions need not be determined but are fixed from the start. This makes it possible in advantageous manner to adjust the full blood flow very rapidly in dependence upon the donor or blood pressure and even change it during a separation.

The invention excludes from the start erroneous settings of the separation parameters such that the speed of the centrifuge is so unfavourable for a selected full blood flow that one of the desired fractions does not even accumulate.

In addition, with the system of the invention the detection of the accumulated blood constituents during the separation is dispensed with, thereby simplifying the system.

DETAILED DESCRIPTION

Figure 1:
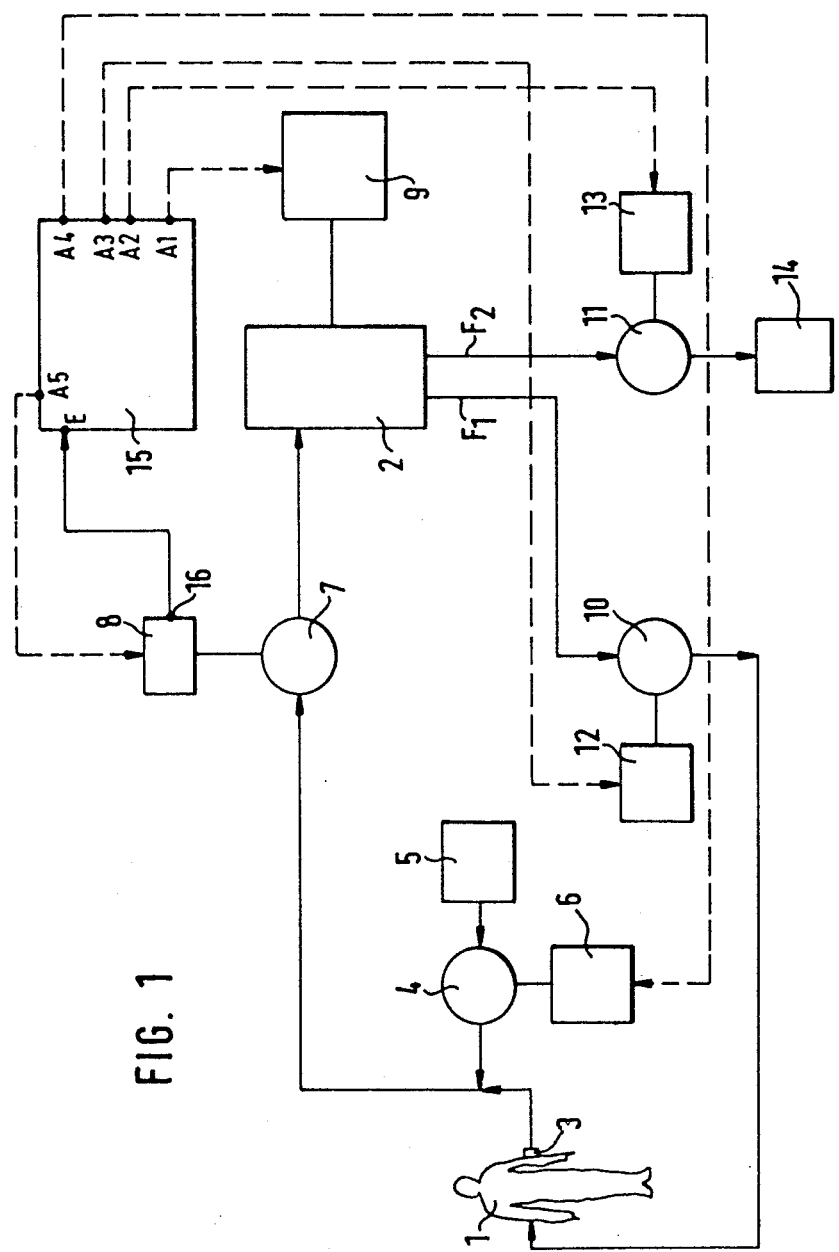
FIG. 1 is a general view of a blood centrifuge system having the control according to the invention.

FIG. 1 shows schematically in the form of a general drawing a system for separating the constituents of the blood withdrawn from a donor 1 "in vivo" in a blood centrifuge 2, including the associated control 15 constructed according to the invention. The system comprises a usual means 3, not shown in detail, for blood extraction on the donor 1 and a pump 4 for supplying anticoagulants stored in a container 5 to the withdrawn blood. The pump 4 has associated therewith a control/regulating means 6 for adjustment of the flow rate of the anticoagulant.

The system further comprises a pump 7, the blood pump, for delivering the withdrawn full blood to the blood centrifuge 2. The blood pump 7 has associated therewith a control/regulating means 8 for setting the flow rate of the full blood.

The drive of the centrifuge 2 comprises a control/regulating means 9 for setting the speed of rotation of the centrifuge.

Provided at the centrifuge are two outlets for withdrawing the separated blood constituents, the blood fractions, i.e. the plasma fraction $F_1$ and the cell fraction $F_2$. Associated with each withdrawal line is a pump 10 and 11. The flow rates of the blood fractions can be set by control/regulating means 12, 13 associated with the respective pumps. Part of the blood fractions, in this case the cell fraction $F_2$, is collected in a container 14 whilst the other part of the blood fractions, the plasma fraction, is returned to the donor. It is also known to return part of the cell fraction to the withdrawn blood again.

The system described above is known from the U.S. patent named at the beginning and described in all detail therein.

To ensure optimum automatic control of the system, a control 15 is provided which as input signal receives indirectly or directly a signal on the flow rate of the full blood generated by a sensor 16. The output of the control acts with a first signal (output A 1) on the control/regulating arrangement 9 for adjusting the speed of rotation of the centrifuge. The outputs A 2 to A 3 are connected to the control/regulating arrangements 12, 13 of the delivery means 10, 11 of the blood fractions $F_1$ and $F_2$. The output A 4 communicates with the control/regulating arrangement 6 of the delivery means 4 of the anticoagulant. The output A 5 is returned to the adjusting means 8 for the full blood.

The transfer function of the control 15 as regards the output A 1 is determined according to the invention such that on changing the full blood flow the speed of rotation of the centrifuge can be changed so that the ratio of the volume parts of the blood fraction separated in the centrifuge per unit time to the volume of the full blood conveyed into the centrifuge in the unit time remains approximately the same ratio before and after a change of the full blood, or expressed mathematically:

$$\frac{\text{Volume (fraction}_n)_t}{\text{Volume (full blood)}_t} = \frac{\text{volume (fraction}_n)_{t+\Delta t}}{\text{volume (full blood)}_{t+\Delta t}}$$

To ensure this, according to a further development of the invention the transfer function is advantageously so defined that on a change in the full blood flow and the associated input signal at the input of the control stage the output signal (A1) for adjusting the speed of the centrifuge is proportional to the square root of the newly set full blood flow, i.e.

$$(1)\ \text{Speed (centrifuge)} = c_5 \times \sqrt{\text{flow (full blood)}}.$$

This transfer function ensures an optimum setting of the system parameters in dependence upon the fluctuations in the full blood flow.

As regards the outputs A 2–A 4 the transfer function of the control 15 is so defined that on an alteration of the full blood flow in addition output signals for the setting of the flow rates of anticoagulants and all the blood fractions can be generated which are proportional to the magnitude of the full blood flow, or expressed mathematically (2) Flow (anticoagulant)=$C_4$x flow (full blood)
(3) Flow (fraction$_n$)=$C_n$x flow (full blood) n>2=index of the fraction.

This ensures a comprehensive optimum and flexible setting of the system.

The proportionality factors $C_4$, $C_5$, $C_n$, the so-called coupling constants, are preset and in the control permanently entered (stored) in the form of digital or analog quantities and thus can inform the associated control/regulating arrangements of the desired proportionalities for the operation.

The control 15 is made up in such a manner that the flow rate of the anticoagulant or of the individual blood fractions or the speed of rotation of the centrifuge are each individually variable uncoupled from the other parameters, in particular without reaction on the full blood flow, in that the associated coupling constant is varied and the changed value stored in the control stage, i.e.
(4) Flow (anticoagulant)=$C_4'$ x flow (full blood)
(5) Flow (fraction)=$C_n'$ x flow (full blood)
(6) Speed (centrifuge)=$C_5'$ x $$(6) \text{ Speed (centrifuge)} = C_5' \times \sqrt{\text{flow (full blood)}}.$$

A change for example in the cell flow then manifests itself for example as a change in the associated coupling constant.

Figure 2:
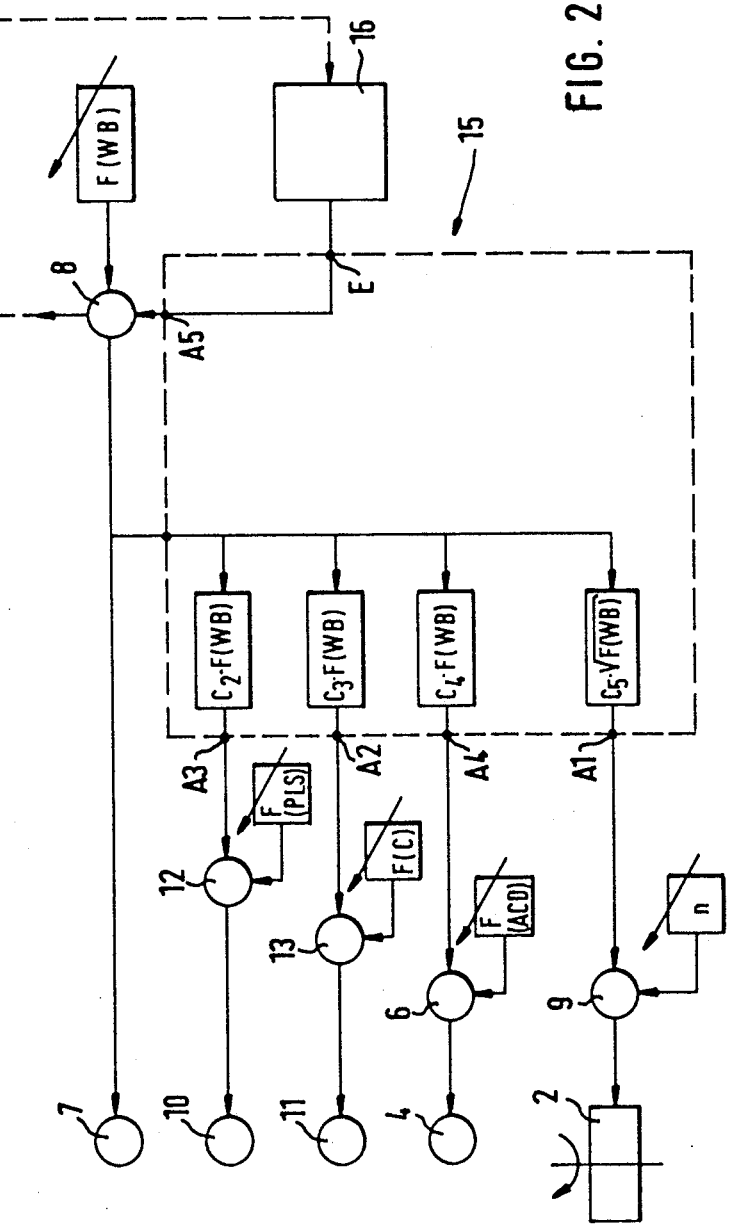
FIG. 2 is a general view of the basic makeup of a parameter coupling between full blood flow and the flow rates of the anticoagulant, the blood fractions and the centrifuge speed of rotation.

These relationships are shown schematically in FIG. 2 using the symbols of control technology. The meaning of the symbols in this Figure are
F (WB) full blood flow
$C_2$ coupling constant for the plasma flow F (PLS)
$C_3$ coupling constant for the cell flow F (C)
$C_4$ coupling constant for the anticoagulant flow F (ACD)
$C_5$ coupling constant for the centrifuge speed of rotation n.

In the left part of FIG. 2 the pumps 7, 10, 11 and 4 are shown. The boxes having a diagonal arrow are the control/regulating means 6, 8, 9, 12, 13 associated with the pumps. In the other boxes the products indicated below of the full blood flow and the coupling constants are formed and represent the magnitude of the flows to be set and the centrifuge speed, i.e. the desired values for the control/regulating means of the pumps and centrifuge motor:
F(PLS)=$C_2$·F(WB) plasma flow
F(C)=$C_3$·F(WB) cell flow
F(ACD)=$C_4$ F(WB) anticoagulant flow $$n = C_5 \cdot \sqrt{F(WB)}$$

The reference variable for setting the full blood flow itself is expediently taken from an input pressure control (with the sensor 16) as will be explained hereinafter.

The makeup of the system and the control can be with conventional components. Thus, the delivery means 7 and 10, 11 and 4 for the full blood and blood fractions and for anticoagulant are peristaltically operating hose pumps in which the flow is set with a control or regulating means for the speed of rotation of the pumps.

The means 7 for delivering the full blood is preferably a pump (blood pump) which can be regulated to constant input pressure and the pressure sensor of which is simultaneously the sensor 16 for the flow rate of the full blood. Such pumps prevent collapse of the blood withdrawal tube on a drop of the blood pressure of the donor and unreduced speed of rotation (withdrawal rate). The blood pump has in such cases an underlying control system 8 for a change of the flow rate of the full blood which is constructed such that it sets the flow rate of the full blood, and coupled thereto the other system parameters, so that it corresponds to the blood volume offered at the input of the blood pump per unit time.

Conveniently, a pressure sensor is provided for the input pressure of the blood pump and forms the actual value signal for the control system.

The desired value of the control system may be a predetermined pressure value so that the control system sets the full blood flow of the blood pump in such a manner that the input pressure assumes a constant value corresponding to the desired value. A predetermined desired value range may also be associated with the control system so that the flow of the blood pump can be set to keep the input pressure within the desired value range.

The control can basically be constructed from fixedly wired computing members. It is however advantageous to implement the control 15 by a microprocessor operating as digital program controller, this considerably increasing the flexibility and the variation range of the adjustment possibilities. Such a system is shown schematically in FIG. 3 and the fundamentals thereof will now be explained.

After switching on the system in particular the values on the full blood flow F(WB)—values 1.1—and the coupling constants $C_2$ and $C_5$ are permanently stored in a digital memory.

In the so-called separation program part the following operating parameters are calculated with the aid of these predetermined stored values by the microprocessor:

1.2 plasma flow F(PLS) = $C_2 \cdot$ F(WB)
1.3 cell flow F(C) = $C_3 \cdot$ F(WB)
1.4 anticoagulant flow F(ACD) = $C_4 \cdot$ F(WB)

1.5 centrifuge speed $n = C_5 \cdot \sqrt{F(WB)}$.

Thereafter, the microprocessor furnishes corresponding outputs via following digital/analog converters to the control/regulating arrangements 12, 13, 6, 9 so that by adjustment of the pumps 10, 11, 4 and the motor of the centrifuge 2 the corresponding flows and the calculated speed are set. This separation program corresponds to the illustration of FIG. 2.

Going beyond the separation program the microprocessor system provides a program part referred to as "parameter coupling to the full blood flow".

Figure 3:
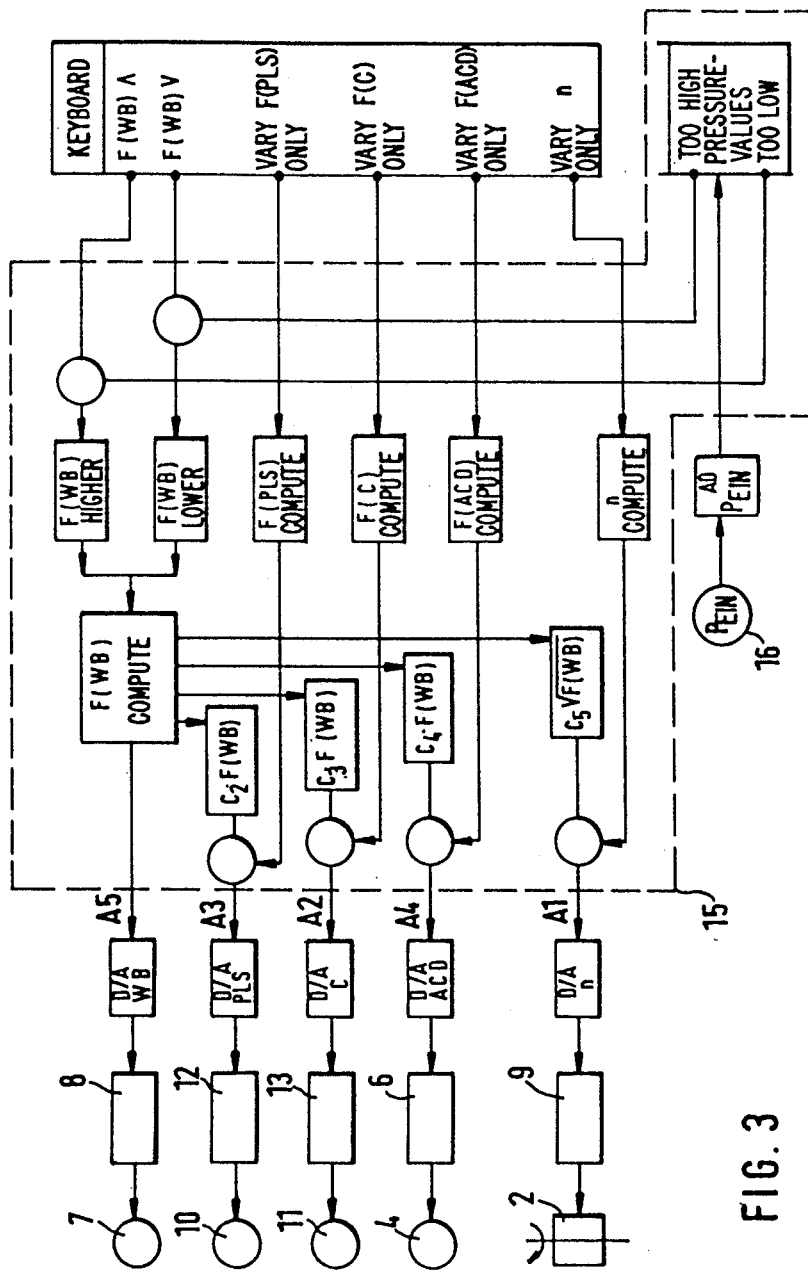
FIG. 3 is a schematic representation of the basic makeup of a digital control stage formed by a microprocessor.

Via a keyboard input for the microprocessor system—upper row in FIG. 3, right portion—it is possible to change the full blood flow for the separation program:

2.1 F(WB)→F'(WB) and: F(WB) = F'(WB) is stored.

Consequently, as shown in the upper row of FIG. 3 in each case the changed full blood flow F(WB) is calculated, passed to the controller 8 of the blood pump and stored as new calculated value F(WB). With the aid of the stored coupling constants $C_2$, $C_3$, $C_4$, $C_5$ directly thereafter the remaining operating parameters are also changed:

2.2 $F(PLS) \rightarrow F'(PLS) = C_2 \cdot F(WB)$
and:

2.3 $F(C) \rightarrow F'(C) = C_3 \cdot F(WB)$
and:

2.4 $F(ACD) \rightarrow F'(ACD) = C_4 \cdot F(WB)$ 2.5 $n \rightarrow n' = C_5 \cdot \sqrt{F(WB)}$ Such changes in the full blood flow can be carried out as often as desired during the separation program and in each case the last parameter set is carried out according to 2.1 to 2.5 by the microprocessor in the separation program.

The microprocessor system also comprises a program part "parameter change without parameter coupling".

Via the keyboard input (rows 2 to 5) it is possible to change individually the following separation parameters without this having any influence on any other operating parameter.

3.2 Change in the plasma flow $F(PLS) \rightarrow F'(PLA) = C_2' \cdot F(WB)$

This is stored as new coupling constant by the microprocessor system after the change $C_2 = C_2'$;

3.3 or change in the cell flow:

$F(C) \rightarrow F'(C) = C_3' \cdot F(WB)$ and $C_3 = C_3'$ as new coupling constant, 3.4 or change in the anticoagulant flow $F(ACD) \rightarrow F'(ACD) = C_4' \cdot F(WB)$ and $C_4 = C_4'$ as new coupling constant, 3.5 or change in the centrifuge speed $n \rightarrow n' = C_5' \cdot \sqrt{F(WB)}$ and $C_5 = C_5'$ as new coupling constant.

Changes of the operating parameters according to 3.2 to 3.5 can be carried out any combination and in each case the last parameter set is performed by the microprocessor system. "Parameter coupling to the full blood flow" after a parameter change according to one of the steps 3.2 to 3.5 is carried out with the last parameter set stored $C_2, C_3, C_4, C_5$ in accordance with the aforementioned steps 2.2 to 2.5.

The "parameter coupling to the full blood flow" is conveniently effected with a pressure control of the full blood flow illustrated in FIG. 3 in the right lower portion of the drawing and referred to as optional input-pressure-controlled parameter coupling. A pressure sensor 16 is provided which detects the input pressure and enters it via an analog/digital converter into the microprocessor.

Three variants of this coupling are conceivable.

4.1 Only reduced pressure control (so-called high flow monitoring).

In this variant by means of a pressure measurement it is merely supervised whether the blood flow set is high.

The following method steps (cycle) are carried out:

4.1.1 After the start of the separation program all the pumps and the centrifuge run up to the preset values in accordance with the previously described steps.

4.1.2 The input pressure is measured and monitored by a microprocessor system or other electronic circuit.

4.1.3 The input pressure $P_{ein}$ drops below an admissible threshold $P_{min}$, i.e. F(WB) is too high.

4.1.4 A new full blood value is calculated $F'(WB) = F(WB) - \Delta F(WB)$
$\Delta F(WB) =$ full blood flow reduction
(one step e.g. 5 ml/min)

4.1.5 Thereafter parameter coupling is made to the value F' (WB) in accordance with the steps 2.2 to 2.5 explained.

4.1.6 A maximum lower limit for F' (WB) should be pre-defined (e.g. F' (WB)>25 ml/min) in order in the event of a high or complete occlusion of the entrance line or withdrawal needle not to allow the value F' (WB)=0 as operating parameter.

4.1.7 The next cycle then starts again with step 4.1.2.

4.2 Full blood flow optimization only in an initial phase In an optimizing phase at the beginning the full blood flow is optimized once (i.e. maximized); after conclusion of this phase it is only monitored whether this flow can be maintained for the duration of the treatment or whether it is to be reduced. In this variant the following steps are carried out:

4.2.1 After the start of the separation program all the pumps and the centrifuge run up to the preset values in accordance with the previously described steps.

4.2.2 The input $P_{ein}$ measured and monitored by a microprocessor system or other electronic circuit.

4.2.3 $P_{ein}$ therefore lies above a predetermined threshold $P_{max}$, i.e. F(WB) is too low.

4.2.4 Calculation of a new full blood flow
$F'WB)=F(WB)+\Delta F(WB)$ 4.2.5 Parameter coupling to the new value F' (WB) in accordance with 2.2 to 2.5.

4.2.6 If $P_{ein} > P_{max}$, continue with 4.2.4

4.2.7 If $P_{ein} > P_{max}$, continue with 4.1.2 (i.e. flow optimization phase completed).

4.3 Continuous full blood flow optimization

In this variant for the duration of the entire treatment the maximum possible full blood flow is regulated.

(Note: If $P_{min} = P_{max}$ and $\Delta F(WB)$ is very small then with the control procedure according to 4.3 a constant input pressure is adjusted)

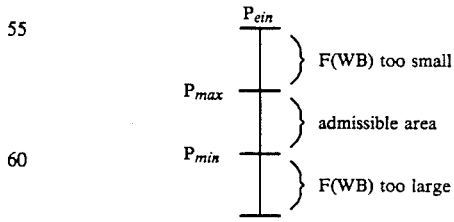

The following method steps are provided:
4.3.1 as 4.1.1
4.3.2 as 4.1.2
4.3.3 as 4.2.3
4.3.4 as 4.2.4

4.3.5 as 4.2.5
4.3.6 as 4.2.6
4.3.7 if $P_{ein} > P_{min}$, continues with 4.3.3
4.3.8 if $P_{ein} > P_{min}$: $F'(WB) = F(WB) - \Delta F(WB)$
4.3.9 Parameter coupling to the new value of $F(WB)$ 2.2. to 2.5.
4.3.10 as 4.1.6
4.3.11 continues with 4.3.3 (i.e. continuous flow optimization)

The microprocessor thus also operates for optimum setting of the other parameters for the full blood supply within the control cycle.

I claim:

1. A method for separating constituents of whole blood which is withdrawn from a donor, mixed with anticoagulant, and supplied to a speed-adjustable blood centrifuge from which blood constituents are withdrawn and thereafter partially collected and partially returned to the donor, which method comprises:
   measuring flow rates of the whole blood, anticoagulant and of the blood fractions; and
   adjusting a speed of rotation of the centrifuge upon a variation of the flow rate of whole blood according to transition function, which transition function is chosen such that a ratio of volume parts of the blood fractions separated in the centrifuge per unit time to a volume of the whole blood and anticoagulant supplied to the centrifuge in a unit time is approximately the same before an after the variation in the flow rate of whole blood.

2. The method according to claim 1, wherein upon a change in thee flow rate of whole blood the flow rate of the anticoagulant into the centrifuge and the flow rate of each blood fraction out of the centrifuge are adjusted such that the flow rates have approximately the same ratio to the flow rate of whole blood as before said change.

3. The method according to claim 1, wherein the transition function is the square root of the flow rate of whole blood occurring after said variation.

4. The method according to claim 1, wherein a proportionally factor for the transition function and the flow rates of the anticoagulant and whole blood fractions are predetermined and stored.

5. The method according to claim 1, wherein the flow rate of the anticoagulants and individual blood fractions and the speed of rotation of the centrifuge are each individually variable and without effect on the flow of whole blood, and the resulting ratio is changed and stored.

6. The method according to claim 1, wherein the flow rate of the whole blood is separately regulated and corresponds to a volume supplied per unit time at an inlet of a blood pump.

7. An apparatus for separating constituents of whole blood withdrawn from a donor, said apparatus comprising:
   a blood centrifuge with means associated for blood withdrawal, delivery of anticoagulant, delivery of withdrawn blood to the blood centrifuge, and for separating constituents which are partially collected and partially returned to the donor;
   means for adjusting flow rates of the anticoagulant, the whole blood and the blood fractions and a speed of rotation of rotation of the centrifuge; and
   a sensor means for detecting the flow rate of the whole blood, a signal from said sensor being switched to a control stage which has a transition function and whose output is connected to the adjusting means, wherein the transition function of the control stage is chosen such that on a variation in a flow of whole blood an associated input signal at an input of the control stage and an output signal for setting a speed of rotation of the centrifuge changes such that a ratio of volume parts of blood fractions separated in the centrifuge per unit time to volume of whole blood conveyed in the unit time into the centrifuge is approximately the same ratio before and after the variation in the flow of whole blood.

8. The apparatus according to claim 7, wherein the transition function of the control stage is the square root of the flow rate of whole blood occurring after the variation.

9. The apparatus according to claim 7, wherein the control stage is connected to the means for delivering the anticoagulant and blood fractions and controls said delivery means such that on a variation in the flow of whole blood the flow rate of the anticoagulant into the centrifuge and the flow rate of each blood fraction out of the centrifuge has approximately the same respective ratio to the flow rate of whole blood before and after the variation in blood flow.

10. The apparatus according to claim 9, wherein numerical values for said ratios are predetermined and stored as digital or analog quantities in the control stage.

11. The apparatus according to claim 10, wherein said numerical values are assigned to the control stage individually and are independent from one another.

12. The apparatus according to claim 7, wherein the control stage is a microprocessor system.

13. The apparatus according to claim 7, wherein the means for delivering the anticoagulant, the whole blood, and blood fractions are peristaltically operating hose pumps with each of which a control or a regulating means is associated for adjusting the respective flow rates.

14. The apparatus according to claim 7 further comprising a control system utilizing a pump means of delivering the whole blood to change the flow rate of the whole blood, wherein said control system adjusts the flow rate of the whole blood and coupled thereto the flow rates of the anticoagulant and various blood fractions, and an inlet pressure at the pump is adjusted to a constant value.

15. The apparatus according to claim 14, wherein a pressure sensor is provided for the inlet pressure of the pump and forms an actual value signal for the control system.

16. The apparatus according to claim 14, wherein a range for the constant value is predetermined, such that the flow rate of the whole blood is adjusted and the inlet pressure is maintained in the range of the constant value.

* * * * *

UNITED STATES PATENT AND TRADEMARK OFFICE
CERTIFICATE OF CORRECTION

PATENT NO. : 4,968,295

DATED : November 6, 1990

INVENTOR(S) : NEUMANN

It is certified that error appears in the above-identified patent and that said Letters Patent is hereby corrected as shown below:

In claim 1, line 4, delete "constituents" and insert therefore --constituent blood fractions--.

In claim 7, line 7, delete "constituents" and insert therefore --constituent blood fractions--.

Signed and Sealed this

Third Day of March, 1992

Attest:

HARRY F. MANBECK, JR.

*Attesting Officer*     *Commissioner of Patents and Trademarks*